United States Patent [19]

Schmidt et al.

[11] 4,164,611

[45] Aug. 14, 1979

[54] AROMATIC SULFONYL HYDRAZIDES AND SEMICARBAZIDES AS CHEMICAL BLOWING AGENTS

[75] Inventors: Andreas Schmidt; Hugo Illy, both of Reinach; Rudolf Kirchmayr, Aesch, all of Switzerland; André Schmitter, Hegenheim, France

[73] Assignee: Ciba-Geigy Corporation, Ardsley, N.Y.

[21] Appl. No.: 703,878

[22] Filed: Jul. 9, 1976

[30] Foreign Application Priority Data

Jul. 10, 1075 [CH] Switzerland ..................... 9024/75

[51] Int. Cl.² ................ C07C 133/02; C07C 143/825; C08J 9/10
[52] U.S. Cl. ..................................... 521/89; 260/554; 260/556 H; 521/95; 521/120; 521/129; 521/142; 521/145; 521/189
[58] Field of Search ............... 260/554, 556 H, 2.5 R, 260/2.5 N, 2.5 H; 521/89

[56] References Cited

U.S. PATENT DOCUMENTS

| | | | |
|---|---|---|---|
| 2,626,933 | 1/1953 | Lober et al. | 260/556 H X |
| 2,640,853 | 6/1953 | Sundholm | 260/556 H |
| 3,152,176 | 10/1964 | Hunter | 260/554 |
| 3,235,519 | 2/1966 | Hunter | 260/554 X |
| 3,344,182 | 9/1967 | Amidon | 260/554 |
| 3,903,157 | 9/1975 | Hunter | 260/554 |
| 3,925,270 | 12/1975 | Hunter | 260/2.5 H X |
| 3,925,466 | 12/1975 | Hunter | 260/556 H X |
| 3,933,909 | 1/1976 | Herweh | 260/554 |

FOREIGN PATENT DOCUMENTS 720704  12/1954  United Kingdom ............... 260/556 H

*Primary Examiner*—Thomas Waltz
*Attorney, Agent, or Firm*—Karl F. Jorda

[57] ABSTRACT

Aromatic sulfonic acid hydrazides and semicarbazides having a sterically hindered phenol group are usable as blowing agents in the manufacture of foamed plastics articles. On heating to about 200 to 300° C. they are splitting off nitrogen and the residue remaining in the foam acts as stabilizer against thermo-oxidative degradation of the plastic material.

18 Claims, No Drawings

AROMATIC SULFONYL HYDRAZIDES AND SEMICARBAZIDES AS CHEMICAL BLOWING AGENTS

The invention relates to new aromatic sulphonic acid hydrazides and semicarbazides and to their use as blowing agents for the foaming of plastics.

When foaming plastics by the blowing gas process, gases or low-boiling liquids can be dissolved in the polymer under pressure; the polymer then expands when heated in the absence of pressure. The use of pressure can be avoided if chemical blowing agents are employed. These are substances which are stable at normal or slightly elevated temperature, but decompose when heated, eliminating an inert gas such as nitrogen or carbon dioxide. Known examples thereof are azodicarboxylic acid derivatives, carboxylic acid hydrazides, sulphonic acid hydrazides and N-nitrosocarboxylic acid amides. Sulphonic acid semicarbazides have also been proposed for this purpose, in DT-AS No. 1,494,373.

When these blowing agents decompose, a residue, formed from the remainder of the molecule of the blowing agent, is in most cases produced alongside the inert blowing gas. Such a residue can have adverse effects on the foam; for example, it can have a plasticising action, cause a discoloration or bring about physiological disadvantages, for example through having an unpleasant odour.

It was therefore the object of the present invention to provide chemical blowing agents which, on decomposition, form a residue which not only has no adverse effect but, beyond this, exhibits an advantageous effect. The advantageous effect is, in the present case, a stabilising effect against thermo-oxidative aging of the plastic.

Amongst the known chemical compounds it has hitherto not been possible to find any which act simultaneously as blowing agents and as stabilisers. However, it has now proved possible, surprisingly, to find new chemical compounds which possess these properties. Accordingly, the present invention relates to new compounds which can be used both as blowing agents and as stabilisers for plastics. These compounds have the general formula I

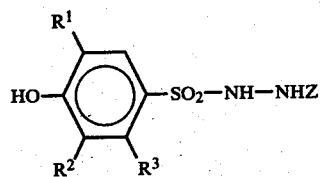

in which $R^1$ and $R^2$ independently of one another denote hydrogen or an alkyl group with 1–4 C atoms, but at least one of the two substituents denotes alkyl, $R^3$ denotes hydrogen or alkyl with 1–4 C atoms and Z denotes hydrogen or $—CONH_2$.

When $R^1$, $R^2$ or $R^3$ denote alkyl with 1–4 C atoms, they can be a branched or unbranched alkyl group, for example methyl, ethyl, propyl, isopropyl, sec.-butyl or tert.-butyl.

Preferred compounds of the formula I are those in which $R^1$ and $R^2$ denote alkyl with 1–4 C atoms, especially methyl, isopropyl or tert.-butyl, $R^3$ denotes hydrogen and Z denotes $—CONH_2$.

Examples of compounds of the formula I which can be used according to the invention as blowing agents and stabilisers are the following: 3,5-dimethyl-4-hydroxybenzenesulphonylhydrazide, 3,5-dimethyl-4-hydroxybenzenesulphonylsemicarbazide, 3,5-diisopropyl-4-hydroxybenzenesulphonylhydrazide, 3-methyl-5-isopropyl-4-hydroxybenzenesulphonylsemicarbazide, 3,5-di-tert.-butyl-4-hydroxybenzenesulphonylsemicarbazide, 3,5-di-tert.-butyl-4-hydroxybenzenesulphonylhydrazide, 3-tert.butyl-5-isopropyl-4-hydroxybenzenesulphonylhydrazide, 3-tert.butyl-5-methyl-4-hydroxybenzenesulphonylsemicarbazide, 3,5-di-tert.-butyl-6-methyl-4-hydroxybenzenesulphonylsemicarbazide, 3,5-di-tert.-butyl-6-isopropyl-4-hydroxybenzenesulphonylsemicarbazide, 3,5-diisopropyl-6-methyl-4-hydroxybenzenesulphonylsemicarbazide and 3,5-diisopropyl-6-methyl-4-hydroxybenzenesulphonylhydrazide.

These compounds are crystalline substances which decompose at temperatures of about 180°–280° C., eliminating inert gases, above all eliminating nitrogen.

Both the compounds of the formula I and their decomposition residues have a stabilising action against the thermooxidative aging of plastics.

The compounds of the formula I are advantageously manufactured by reacting the sulphochlorides II

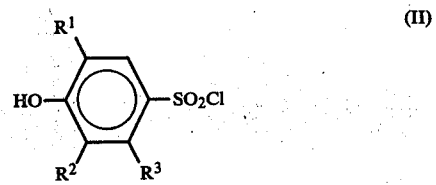

with hydrazine or with semicarbazide in accordance with methods which are in themselves known. The sulphonylsemicarbazides of the formula I, $Z=—CONH_2$, can also be manufactured from the sulphonylhydrazides I, $Z=H$, by reaction with cyanic acid. For this purpose, the method of reacting acid addition salts of the hydrazides with alkali metal cyanates is used, above all.

The starting materials of the formula II can be manufactured in accordance with the methods described in Helv. Chim. Acta 27, 678 (1944) and in J. Org. Chem. 31, 2,674 (1966).

The compounds according to the invention, of the formula I, are in principle suitable for use as blowing agents for all foamable plastics. These can be thermoplastic polymers, such as, for example, homopolymers or copolymers of olefines, styrene, vinyl chloride or vinylidene chloride, or they can be thermoplastic polycondensation products, such as polyethers, polyesters, polycarbonates, polyacetals, or polysulphones. However, they can also be thermosetting plastics, such as epoxide resins or phenolic resins.

However, because of the stabilising action, the use of the compounds is of particular interest for those plastics which are sensitive to thermo-oxidative factors. These are, above all, polyolefines, for example polypropylene and polyethylene, polystyrene and styrene copolymers, such as are known, for example, under the name ABS polymers, polyvinyl chloride, polyamides, for example polycaproclactam, polycarbonates, for example the polycarbonate of 4,4′-dihydroxydiphenylpropane-2,2, or polyphenylene oxides, for example poly-2,6-dimethylphenylene oxide, and polysulphones.

The addition of the compounds of the formula I can be effected in accordance with the methods customary for chemical blowing agents. These include cold mixing of the comminuted plastic with the blowing agent in a suitable mixing apparatus for the purpose. The blowing agent can, in this case, be employed dry or as a solution in a low-boiling solvent, which is subsequently evaporated. In the case of plastics with a broad temperature range of the plastic state, the blowing agent can also be mixed warm with the plasticised plastic, for example on a mixing mill which can be heated, or in an internal kneader which can be heated. In this respect it is advantageous that the blowing agents of the formula I only decompose at a relatively high temperature. Finally, in isolated cases, it is also possible to add the blowing agent before or during the polymerisation, provided the latter is carried out below the decomposition temperature.

The mixtures of a plastic with the blowing agent, prepared in this way, are substantially storage-stable. They can be foamed by heating to temperatures above the decomposition temperature of the blowing agent. This can be done in open or closed moulds, batchwise or continuously; the latter method can be used, for example, in an extruder.

If it is intended to use the blowing agents for foaming plastics which are processed at temperatures below the decomposition temperature of the blowing agent, so-called kickers can be added. These are catalytically active substances which lower the decomposition temperature. Such kickers are commonly used, above all, when foaming PVC; for example, zinc salts, cadmium salts and barium salts of stearic acid are used for this purpose. Such compounds can also be combined with the compounds of the formula I.

In the case of thermosetting plastics, the blowing agent can be added to a liquid or plastic intermediate stage. Where multi-component systems are concerned, the blowing agent is advantageously mixed with one component before adding the second component. Foaming then takes place simultaneously with the thermal curing of the thermosetting resin.

The amount of the blowing agent added depends above all on the desired degree of foaming, that is to say on the desired density of the foam. It further depends on the particular gas yield of the blowing agent used. In general, the amounts added are about 0.1 to 5% by weight.

The amounts required for foaming also suffice for their action as a stabiliser. However, in certain cases it can be advantageous additionally also to introduce other known stabilisers, for example light stabilisers for polyolefines or polyamides, acid acceptors for polyvinyl chloride or metal deactivators in the case of cable-coating. Furthermore, other agents customary and known in plastics technology can be added, such as, for example, plasticisers, lubricants, fillers, pigments, flame-proofing agents, foam regulators or antistatic agents.

The examples which follow describe the preparation and use of the new compounds.

EXAMPLE 1

3,5-Dimethyl-4-hydroxybenzenesulphonylsemicarbazide 11 g (0.05 mol) of 3,5-dimethyl-4-hydroxybenzenesulphonic acid chloride and 6 g (0.05mol) of semicarbazide hydrochloride are first introduced into 50 ml of dimethylacetamide. 10 ml of 10 N sodium hydroxide solution are added dropwise to this white suspension over the course of 15 minutes at 40° C., whilst stirring. Since the reaction is exothermic, slight cooling must be applied. The mixture is then stirred for a further 4 hours at 40° C. After cooling to 0° C., the sodium chloride which has precipitated is filtered off and the filtrate is concentrated completely under reduced pressure. The residue is dissolved in a small amount of water and is cooled to 0°–5° C. Hereupon, 3.5-dimethyl-4-hydroxybenzenesulphonylsemicarbazide, of melting point 243° C. (with decomposition), crystallises out.

EXAMPLE 2

3,5-Dimethyl-4-hydroxybenzenesulphonic acid hydrazide 15.0 g (0.3 mol) of hydrazine hydrate are first introduced into 60 ml of dimethylacetamide. 22 g (0.1 mol) of 3,5-dimethyl-4-hydroxybenzenesulfonic acid chloride dissolved in 60 ml of dioxane are added dropwise to this solution over the course of 15 minutes. This causes the temperature to rise to 90° C., at which level it is maintained by slight cooling. The mixture is allowed to react for a further 90 minutes and is then completely concentrated under reduced pressure. The residue is recrystallised first from a little water and then from isopropanol. This gives 3,5-dimethyl-4-hydroxybenzenesulphonic acid hydrazide, which melts at 186° C. (with decomposition).

EXAMPLE 3

3,5-Diisopropyl-4-hydroxybenzenesulphonic acid semicarbazide 66.2 g of 3,5-diisopropyl-4-hydroxybenzenesulphochloride are dissolved in 120 ml of dimethylacetamide. 33.4 g of semicarbazide hydrochloride are added to the solution, and a solution of 24 g of NaOH in 40 ml of water is slowly added dropwise, whilst stirring. The mixture is then stirred for 3 hours at 40° C., the NaCl which has separated out is filtered off, and the filtrate is evaporated in vacuo. The crystalline residue is recrystallised from acetonitrile; the product obtained melts at 210° C., with decomposition.

Analysis $C_{13}H_{19}N_3O_4S$; Found. C 49.73%; H 6.80%; N 13.28%; S 10.40%; Calculated. 49.83%; 6.21%; 13.41%; 10.23%.

EXAMPLE 4

3,5-Diisopropyl-4-hydroxybenzenesulphonic acid hydrazide

A solution of 69 g of 3,5-diisopropyl-4-hydroxybenzenesulphochloride in 300 ml of benzene is added dropwise to 25 g of hydrazide hydrate, whilst cooling with an ice bath and stirring, the addition being made in such a way that the temperature does not exceed 15° C. The mixture is then stirred for 3 hours at room temperature. The crude hydrazide is obtained as a soft mass, from which the supernatant benzene is decanted. It can be purified by crystallisation from acetone.

EXAMPLE 5

20 g of polypropylene and 1 g of 3,5-dimethyl-4-hydroxybenzenesulphonylsemicarbazide and 0.2 g of silicone oil are mixed in a drum mixer. The use of the silicone oil ensures that the finely ground blowing agent adheres well to the granules and is uniformly distributed in the mixture.

The tool used for foaming consists of a piston which moves in a cylinder, under the pressure of a small laboratory press. This cylinder can be brought into contact with the free atmosphere through a channel, or can be brought into contact with a mould. The channel is sealed or opened by means of a plug.

The mixture prepared for foaming is introduced into the cylinder, which is heated to 20° above the decomposition point of the blowing agent. The channel is sealed with the plug. A slight pressure is exerted on the piston by means of the laboratory press. The mixture heats up to above the decomposition temperature of the blowing agent and after 5 minutes the channel is opened by withdrawing the plug. The mixture is forced through the channel by increasing the pressure acting on the piston. On leaving the tool, a strand-shaped foam moulding is formed, the appearance, colour, pore structure and degree of foaming of which are assessed visually.

The softening range of the foam is determined by means of differential thermo-analysis and is compared with the softening range of non-foamed polypropylene. This provides information regarding possible degradation or stabilisation of the polymer by the blowing agent or its decomposition products.

When foaming polypropylene with the compound according to Example 1 at 210° C., a polypropylene foam with fine pores is obtained. The foam shows no change in colour compared to non-foamed polypropylene. The softening range of the foam thus obtained is 150°–167° C., whilst the softening range of non-foamed polypropylene is about 145°–165° C.

EXAMPLE 6

100 g of a polystyrene of high impact strength, stabilised with 0.5% of octadecyl β-(3,5-di-tert.-butyl-4-hydroxyphenyl)-propionate as an antioxidant, are homogeneously mixed, as a powder, with 0.6 g of 3,5-diisopropyl-4-hydroxybenzenesulphonic acid semicarbazide (product of Example 3).

5.1 g of this mixture are introduced into a cylindrical aluminium mould of 11 cm³ capacity. The mould is closed with a screw lid and is placed in an oven preheated to 280° C. After 15 minutes, the mould is taken out of the oven, and after cooling it is opened. A homogeneous foam with fine pores is obtained.

Equally satisfactory foaming is achieved with the same blowing agent and the following substrates, under the same or slightly modified experimental conditions:

High density polyethylene, stabilised with 0.1% of the abovementioned antioxidant, oven temperature 375° C., residence time 9 minutes.

Unstabilised polybutylene terephthalate, oven temperature 320° C., residence time in the oven 12 minutes.

Polycarbonate (based on bisphenol A), unstabilised, oven temperature 340°, residence time 12 minutes.

EXAMPLE 7

2 kg of polypropylene granules of melt index 2 are homogeneously mixed first with 2 g of butyl stearate as an adhesion promoter and then with 20 g of powdered 3,5-diisopropyl-4-hydroxybenzenesulphonic acid semicarbazide (product of Example 3). The mixture is plasticised under pressure in an injection molding machine (type Arburg 221/150) and is injected into moulds which have been kept at 20° C. The temperatures in the injection moulding machine are 200/240/240° C. and the cycle time is 90 seconds. The foam obtained has a fine and uniform cell structure.

EXAMPLE 8

100 g of unstabilised polypropylene powder ("Propathene HF 20" of Messrs. Imp. Chem. Ind. Ltd.) are mixed with 0.6 g of one of the blowing agents mentioned in the table and with 0.2 g of 2,6-di-tert.-butyl-para-cresol as a processing stabiliser.

5.5 g, at a time, of the mixture are introduced into a cylindrical aluminium mould which has a volume of 10cm³ and can be closed with a screw lid, and the mould is closed and placed in an oven at 375° C. for 12 minutes.

After cooling with water, the foamed test specimen is taken out and subjected to artificial aging in a circulating air oven heated to 150° C., until incipient decomposition is clearly recognisable. p-Toluenesulphonylsemicarbazide, a commercially available blowing agent, was used for comparison.

Table:

| Blowing agent | Time to reach incipient decomposition |
|---|---|
| 3,5-Dimethyl-4-hydroxybenzene-sulphonylsemicarbazide (Example 1) | 5 days |
| 3,5-Diisopropyl-4-hydroxybenzene-sulphonylsemicarbazide (Example 3) | >7 days |
| p-Toluenesulphonylsemicarbazide (comparison) | 2 days |

What is claimed is:

1. A compound of the formula I

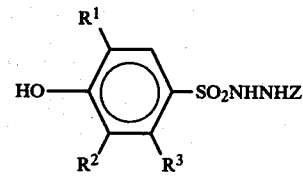

in which $R^1$ and $R^2$ independently of one another denote hydrogen or alkyl with 1–4 C atoms, but at least one of the two substituents denotes alkyl, $R^3$ denotes hydrogen or alkyl with 1–4 C atoms and Z denotes hydrogen or —CONH₂.

2. A compound according to claim 1, of the formula I, in which $R^1$ and $R^2$ denote alkyl with 1–4 C atoms and $R^3$ is hydrogen.

3. A compound according to claim 1, of the formula I, in which Z denotes —CONH₂.

4. A compound according to claim 3, of the formula I, in which $R^1$ and $R^2$ independently of one another denote methyl or isopropyl and $R^3$ denotes hydrogen.

5. The compound 3,5-dimethyl-4-hydroxybenzenesulphonylsemicarbazide according to claim 1.

6. The compound 3,5-diisopropyl-4-hydroxybenzenesulphonylsemicarbazide according to claim 1.

7. The compound 3,5-dimethyl-4-hydroxybenzenesulphonylhydrazide according to claim 1.

8. In a process for foaming a plastic with a foaming agent, the improvement wherein said foaming agent, which at the same time functions as a stabilizer against the thermo-oxidative degradation of the plastic, is the compound of claim 1.

9. A process wherein a compound according to claim 8 is used as a blowing agent for foaming a thermoplastic and at the same time as a stabiliser for the latter.

10. A process according to claim 9 for foaming a polyolefine, polystyrene or styrene copolymer.

11. A process according to claim 9 for foaming polyvinyl chloride or a vinyl chloride copolymer.

12. A process according to claim 9 for foaming a polyamide, polycarbonate or polyphenylene oxide.

13. A foamable composition, which contains a plastic and 0.5 to 5% by weight of a compound of claim 1, which acts both as a blowing agent and as a stabiliser.

14. A foamable composition according to claim 13, wherein the plastic is a thermoplastic.

15. A foamable composition according to claim 14, wherein the plastic is a polyolefine, polystyrene or styrene copolymer.

16. A foamable composition according to claim 14, wherein the plastic is a homopolyer or copolymer of vinyl chloride.

17. A foamable composition according to claim 14, wherein the plastic is a polyamide, polycarbonate or polyphenylene oxide.

18. A foamable composition according to claim 14, which contains other customary and known additives in addition to the blowing agent.

* * * * *